(12) United States Patent
Mannari et al.

(10) Patent No.: US 11,614,432 B2
(45) Date of Patent: Mar. 28, 2023

(54) ADAPTIVE SENSOR TEMPERATURE CONTROL FOR FAST RECOVERY

(71) Applicant: International Business Machines Corporation, Armonk, NY (US)

(72) Inventors: Alberto Mannari, San Jose, CA (US); Andrea Fasoli, San Jose, CA (US); Aminat Adebiyi, San Jose, CA (US); Mohammed Abdi, San Jose, CA (US); Ronald Robert Labby, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 501 days.

(21) Appl. No.: 16/550,611

(22) Filed: Aug. 26, 2019

(65) Prior Publication Data

US 2021/0063372 A1    Mar. 4, 2021

(51) Int. Cl.
*G01N 33/00*   (2006.01)
*G01N 27/22*   (2006.01)

(52) U.S. Cl.
CPC ....... *G01N 33/0073* (2013.01); *G01N 27/227* (2013.01)

(58) Field of Classification Search
CPC .......................... G01N 33/0073; G01N 27/227
See application file for complete search history.

(56) References Cited

U.S. PATENT DOCUMENTS

| | | | |
|---|---|---|---|
| 6,060,025 A * | 5/2000 | Pasquariello | G01N 27/16 204/406 |
| 8,884,382 B2 | 11/2014 | Stetter et al. | |
| 9,632,057 B2 | 4/2017 | Myung et al. | |
| 10,139,382 B2 | 11/2018 | Motayed et al. | |
| 10,191,023 B2 * | 1/2019 | Bäther | G01N 33/0009 |
| 2010/0252451 A1 * | 10/2010 | Warburton | G01N 27/404 205/785.5 |
| 2012/0161796 A1 | 6/2012 | Smith et al. | |
| 2017/0016866 A1 | 1/2017 | Chey et al. | |

(Continued)

FOREIGN PATENT DOCUMENTS

EP    1736768 A1    12/2006

OTHER PUBLICATIONS

Bur, Selective Enhancement of Gas Sensitive Field Effect Transistors by Dynamic Operation, Linkoping University, Dissertation No. 1644, Chapter 4, Section 4.2 (Temperature Modulation) (2015).

*Primary Examiner* — Yoshihisa Ishizuka
*Assistant Examiner* — Christopher J Gassen
(74) *Attorney, Agent, or Firm* — Karen Canaan; CanaanLaw, P.C.

(57) ABSTRACT

Provided is a gas sensor system with a gas sensor, and a microprocessor programmed to control the gas sensor with at least two operational modes. The first operational mode controls the gas sensor from a baseline level through analyte detection. Upon initiation of the recovery phase after analyte withdrawal, the gas sensor system switches to the second operational mode, which changes conditions of the gas sensor to (i) accelerate removal of the analyte from the gas sensor and (ii) accelerate recovery of the gas sensor output towards the baseline level. When no further analyte is detected, the gas sensor switches back to the first operational mode or to an additional operational mode to complete recovery.

17 Claims, 5 Drawing Sheets

(56) References Cited

U.S. PATENT DOCUMENTS

| | | | |
|---|---|---|---|
| 2017/0322171 A1 | 11/2017 | Bather et al. | |
| 2018/0088101 A1* | 3/2018 | Hinshaw | G01N 33/0014 |
| 2018/0306136 A1* | 10/2018 | Mitsuno | F02D 41/1477 |
| 2019/0017981 A1* | 1/2019 | Dutta | G01N 33/0054 |
| 2019/0025271 A1* | 1/2019 | Yan | G01N 33/0027 |
| 2019/0156600 A1* | 5/2019 | Potyrailo | G07C 5/0816 |
| 2019/0204265 A1* | 7/2019 | Stowell | G01N 33/0047 |
| 2019/0212313 A1* | 7/2019 | Christenson | G01N 33/0031 |

\* cited by examiner

ADAPTIVE SENSOR TEMPERATURE CONTROL FOR FAST RECOVERY

TECHNICAL FIELD

The present invention relates generally to gas sensors, and more specifically to an adaptive sensor system that is programmed to optimize the conditions of a gas sensor for both sensing performance and recovery time.

BACKGROUND OF THE INVENTION

Metal oxide semiconductor (MOS) sensors are gas sensors with a metal oxide surface that is capable of adsorbing gases. MOS sensors can detect the concentration of many different types of gases by measuring the resistance change of the metal oxide resulting from the adsorption of the gases. In order to trigger a chemical reaction between the metal oxide and the gases, MOS sensors are operated at high temperatures. An optimal sensing temperature for a MOS sensor is selected to maximize the sensitivity response of the sensor to a specific gas or to achieve maximal discrimination selectivity between separate target gases. When exposed to a given gas, the sensor response will require some time to reach a stable value. When the influx of gas is removed, the sensor signal recovers to its original value, albeit over a lengthened timescale. During the recovery time, the sensor does not provide an output representative of the environment to which it is being exposed. While sensing performance and recovery time can be separately optimized by operating the sensor at different temperatures, temperatures that maximize sensing performance typically do not minimize recovery time.

One approach to combine optimization of sensing and recovery is to periodically switch between the optimal temperature for sensing and the optimal temperature for recovery. The problem with this approach is that during the recovery step, the sensing capabilities of the sensor become sub-optimal. During real-time operation, events of interest may occur at any time and if they occur at the time of the scheduled optimized recovery step, the event of interest may be missed. Because a temperature optimized for sensing does not necessarily provide the shortest recovery time, there is a need in the art for a gas sensor system capable of transitioning between different operational temperatures, depending on the situation, i.e., sensing versus recovery.

SUMMARY OF THE INVENTION

The present invention overcomes the need in the art by providing an adaptive gas sensor system that is optimized for both analyte sensing performance and sensor recovery time.

In one embodiment, the present invention provides a gas sensor system comprising at least one transducer and/or gas sensor, the system comprising: a first sub-system that monitors output from the at least one transducer and/or gas sensor in real-time, wherein the output corresponds to concentration levels of a gas of interest; and a second sub-system comprising at least two operational modes that responds to the output in real-time and adjusts at least one of the at least two operational modes to reduce recovery time of the at least one transducer and/or gas sensor, wherein the real-time response includes detecting and responding to a signal change in the output that is indicative of recovery of the at least one transducer and/or gas sensor towards a baseline value.

In another embodiment, the present invention provides a gas sensor system comprising: at least one transducer and/or gas sensor for detecting an analyte; and a microprocessor programmed to control the at least one transducer and/or gas sensor with at least two operational modes, wherein, a first operational mode controls the gas sensor from a baseline level through analyte detection and initiation of a recovery phase upon analyte withdrawal, and a second operational mode temporarily changes conditions of the at least one transducer and/or gas sensor after the initiation of the recovery phase to (i) accelerate removal of the analyte from the at least one transducer and/or gas sensor and (ii) accelerate recovery of the at least one transducer and/or gas sensor output towards the baseline level, wherein the microprocessor switches the at least one transducer and/or gas sensor from the first operational mode to the second operational mode in real-time and the temporary conditions of the second operational mode prevent the at least one transducer and/or gas sensor from detecting the analyte during the second operational mode.

In a further embodiment, the present invention provides a gas sensor system comprising: at least one transducer and/or gas sensor for detecting an analyte; and a microprocessor programmed to control the at least one transducer and/or gas sensor with at least two operating temperatures, wherein, a first operating temperature controls the at least one transducer and/or gas sensor from a baseline level through analyte detection and initiation of a recovery phase upon analyte withdrawal, and a second operating temperature temporarily changes conditions of the at least one transducer and/or gas sensor after the initiation of the recovery phase to (i) accelerate removal of the analyte from the at least one transducer and/or gas sensor and (ii) accelerate recovery of the at least one transducer and/or gas sensor r output towards the baseline level, wherein the microprocessor switches the at least one transducer and/or gas sensor from the first operating temperature to the second operating temperature in real-time and the temporary conditions of the second operating temperature prevent the at least one transducer and/or gas sensor from detecting the analyte while at the second operating temperature.

In a further embodiment, input into the at least one transducer and/or gas sensor is selected from the group consisting of a change in temperature, a change in humidity, an electrical current, a change in pressure, a change in electromagnetic irradiation, and combinations thereof.

In a further embodiment, initiation of the recovery phase of the first operational mode is defined with an algorithmic function selected from the group consisting of a minimum threshold rate of change of an output signal from the gas sensor, a signal output threshold for the analyte, a signal output pattern, a signal output frequency spectrum, and combinations thereof.

In a further embodiment, completion of the temporary conditions of the second operational mode is defined with an algorithmic function selected from the group consisting of a time limitation on recovery after analyte withdrawal, a maximum threshold rate of change of an output signal from the gas sensor, a signal output pattern, a signal output frequency spectrum, and combinations thereof.

In a further embodiment, upon completion of the temporary conditions of the second operational mode, the at least one transducer and/or gas sensor switches back to the first operational mode and/or one or more additional operational modes to complete recovery of the at least one transducer and/or gas sensor towards the baseline level.

In another embodiment, the at least two operational modes of the at least one transducer and/or gas sensor are at least two operating temperatures with different temperature profiles.

In a further embodiment, the at least two operating temperatures have different temperature profiles.

In another embodiment, the different temperature profiles are separate fixed temperature values and/or separate arbitrary waveforms.

In another embodiment, the at least one transducer and/or gas sensor comprises a material selected from the group consisting of metal oxide semiconductors, conducting polymers, non-conducting polymers, carbon nanotubes, oxidized graphene, sulfides, selenides, black phosphorus, phosphorene, germanene, silicone, and combinations thereof.

In a further embodiment, the at least one transducer and/or gas sensor material further comprises an additive selected from the group consisting of platinum, palladium, gold, rhodium, and combinations thereof.

In another embodiment, the gas of interest and/or the analyte is selected from the group consisting of carbon monoxide (CO), carbon dioxide ($CO_2$), nitrogen oxides ($N_xO_y$; x≥0, y≥0), ammonia ($NH_3$), sulfur dioxide ($SO_2$), volatile organic compounds (VOCs), and combinations thereof.

Additional aspects and embodiments of the invention will be provided, without limitation, in the detailed description of the invention that is set forth below.

DETAILED DESCRIPTION OF THE INVENTION

Figure 1:
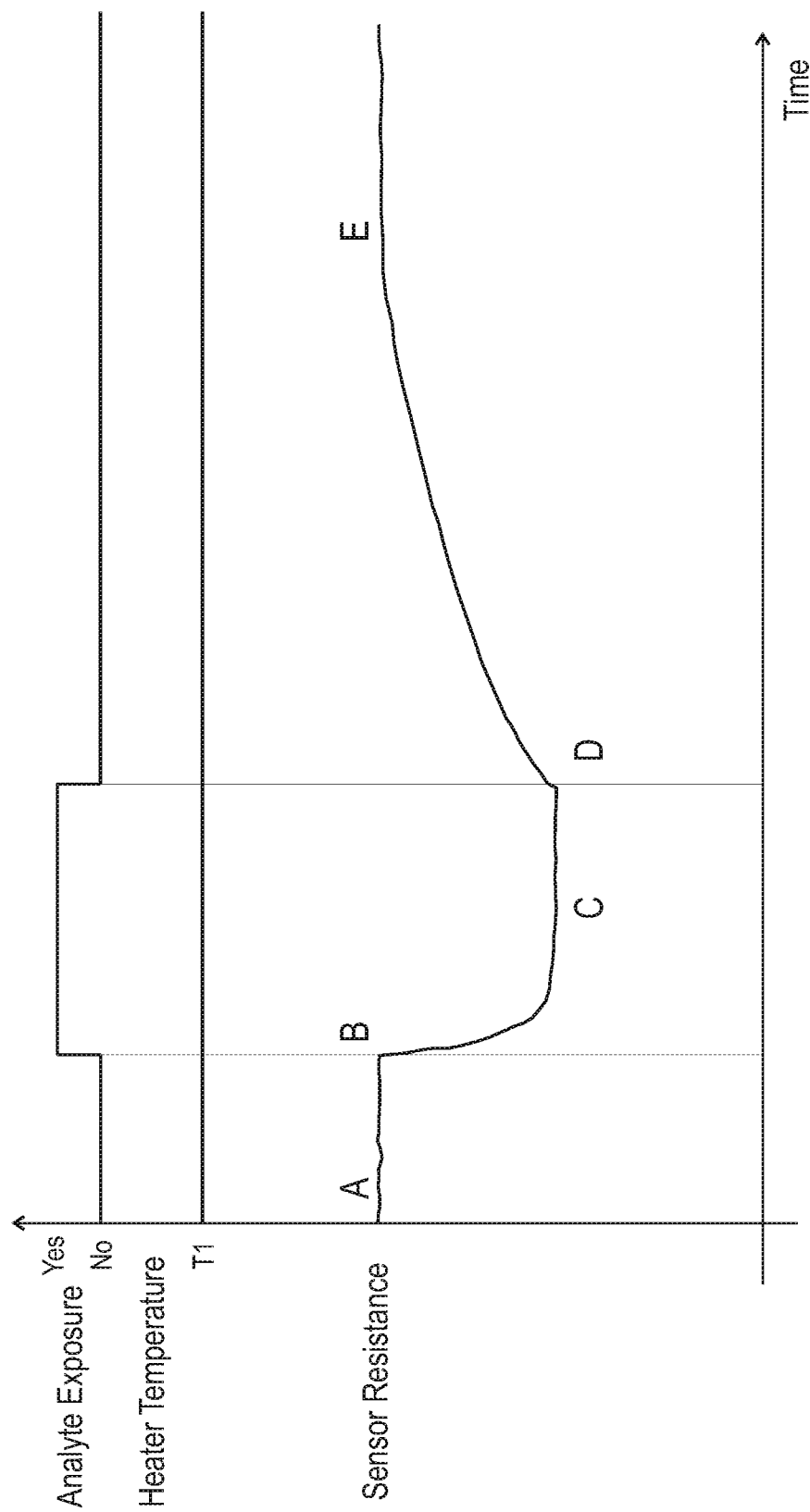
FIG. 1 is a graph showing the analyte exposure, heater temperature, and sensor resistance over time for a conventional gas sensor system.

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

As used herein, the term "gas sensor" or "sensor" is meant to refer to a fixed or portable device that can detect a physical quantity of a gas and convert the quantitative information of that gas into an electrical signal based upon electrical variations caused by the presence of the gas on different materials integrated into the sensor.

As used herein, the term "transducer" is meant to refer to a device that can convert a signal from one form to another. Within the context of the present invention, the gas sensor of the adaptive gas sensor system described herein is also referred to as a transducer because it is capable of converting a chemical detection signal into an electrical output signal based upon the concentration of gas detected.

As used herein, the term "analyte" is meant to refer to a substance of interest that is being detected. Within the context of the present invention, an analyte will generally be a gaseous substance of interest.

The terms "adaptive gas sensor system" and "adaptive sensor system" are used interchangeably throughout to refer to the gas sensor system described herein that uses at least two operational modes to measure analyte exposure and to accelerate sensor recovery.

Gas sensors that may be used with the adaptive sensor system described herein detect gases via gas sensitive materials that chemically react with a target gas and change the resistance of the materials when certain levels of the gas are absorbed or adsorbed on the material. Such gas sensor materials include, without limitation, metal oxide semiconductor (MOS), conducting or non-conducting polymers, carbon nanotubes, oxidized graphene, and combinations thereof.

Gas sensors based on metal oxide semiconductors are applied to detect target gases through redox reactions between the target gases and the oxide surface. This process includes two steps: (1) redox reactions, during which the target gas interacts with the surface of the material leading to an electronic variation of the oxide surface; and (2) the variation is transduced into an electrical resistance variation of the sensors. The variations in the sensing material due to the interaction with the target gas can be also detected for example by measuring the change of capacitance, work function, mass, or optical characteristics.

Metal oxides that may be used as sensing materials for metal oxide semiconductors include both transition and non-transition metal oxides. Transition metal oxides are metal oxides containing elements with more than one oxidation state. Structurally, transition metal oxides are lattice or crystal structures having a central transition metal, which is surrounded by oxygen atoms. Non-transitional metal oxides are metal oxides with only one oxidation state. Examples of some transition and/or non-transitional metal oxides that may be used as the sensing materials in metal oxide semiconductors include, without limitation, AgO (silver oxide), $Al_2O_3$ (aluminum oxide), $CaO_2$ (calcium peroxide), CoO (cobalt oxide), $Co_3O_4$ (cobalt tetraoxide), $Cr_2O_3$ (chromium trioxide), CuO (copper oxide), $Cu_2O_2$ (copper peroxide), FeO (ferrous oxide), $Fe_2O_3$ (ferric oxide), $In_2O_3$ (indium oxide), $K_2O_2$ (potassium peroxide), $LaNiO_3$ (perovskite), $MgO_2$ (magnesium peroxide), $MnO_2$ (manganese dioxide), $Mn_3O_4$ (manganese oxide), $Na_2O_2$ (sodium peroxide), NiO (nickel oxide), $NiCO_2O_4$ (spinel), $SnO_2$ (tin oxide), $TiO_2$ (titanium dioxide), $Ti_2O_3$ (titanium oxide), VO (vanadium oxide), $VO_2$ (vanadium dioxide), $V_2O_5$ (vanadium pentoxide), $WO_3$ (tungsten trioxide), $ZrO_2$ (zirconium dioxide), ZnO (zinc oxide), and $ZnO_2$ (zinc peroxide).

Gas sensors based upon polymers operate similarly to gas sensors based upon metal oxide semiconductors. When the polymer layers are exposed to the vapor of a gas analyte, the physical properties of the polymer layer, such as its mass, electrical, and dielectric properties, change with the gas absorption. The polymers used for polymer-based gas sensors include both conducting polymers and non-conducting polymers.

Examples of conducting polymers that may be used as sensing materials for polymer-based gas sensors include, without limitation, polyacetylene (PA), polyaniline (PAni), polypyrrole (PPy), polythiophene (PTh), poly(3,4-ethylenei-oxythiophene) (PEDOT), and poly(phenylene vinylene) (PPV). Examples of non-conducting polymers that may be used as sensing materials for polymer-based gas sensors include, without limitation, polyimides, polystyrene, polypyrrole, and combinations thereof. To measure the sensor response, non-conducting polymer layers may be coated on mass-sensitive dielectrics, such as QCM (Quartz Crystal Microbalance), SAW (Surface Acoustic Wave), and STW (Surface Transverse Wave). Non-conducting polymers may also be used to make polymer composites that measure the physical changes in sensing materials through electrical measurements.

Gas sensors based upon carbon nanotubes include gas sensitive layers made from single-walled carbon nanotubes (SWCNT) and multi-wall carbon nanotubes (MWCNT). SWCNTs have a one atom thick layer of graphite rolled into a seamless cylinder with a diameter of several nanometers and a length on the order of 1-100μ. MWCNTs consist of multiple layers of graphite wrapped together to form a tube that shares the same central access.

Gas sensors based upon oxidized graphene include gas sensitive layers made from graphene oxide and graphite oxide. Graphene oxide is a single layer of graphite with oxygen functionalities, such as epoxide, carbonyl, carboxyl, and hydroxyl groups. Graphite oxide is a multi-layered oxidized graphene structure.

Other materials that may be used for gas-sensitive films for gas sensors include, without limitation, sulfides, such as molybdenum disulfide ($MoS_2$) and tungsten disulfide ($WS_2$); selenides, such as molybdenum selenide ($MoSe_2$) and tungsten selenide ($WSe_2$); black phosphorus; phosphorene (one atom thick layer of black phosphorous); germanene (one atom thick layer of germanium); and silicone (one atom thick layer of silicon).

In one embodiment, a gas sensor for use in the adaptive sensor system described herein may be based on any one or more of the foregoing classes of gas sensitive materials. For example, based upon the type of gas analyte to be detected, a gas sensor may have a gas sensitive film comprised of a metal oxide semiconductor (MOS), a graphene layer decorated with metal oxide nanoparticles, or a composite film comprising graphene or a metal oxide with one or more conducting polymers.

In another embodiment, an additive may be incorporated into the gas sensing materials to change the properties of the material to enhance sensitivity. Examples of such changes include, without limitation, the rate of gas adsorption onto the material, the capability of the material to perform catalytic reactions, and/or the surface carrier distribution of the material. Examples of additives for gas sensing materials include, without limitation, platinum, palladium, gold, rhodium, and combinations thereof.

The adaptive sensor system described herein may be used to detect any gas that is detected with conventional gas sensors. Examples of such gases include, without limitation, carbon monoxide (CO), carbon dioxide ($CO_2$), nitrogen oxides ($N_xO_y$; x≥0, y≥0), ammonia ($NH_3$), sulfur dioxide ($SO_2$), and volatile organic compounds (VOCs). Nitrogen oxides include, without limitation, nitric oxide (NO), nitrogen dioxide ($NO_2$), nitrous oxide (also known as nitrogen monoxide; $N_2O$), and nitrogen pentoxide ($NO_5$). Examples of VOCs include, without limitation, acetone, ethanol, benzene, ethylene glycol, formaldehyde, methylene chloride, tetrachloroethylene, toluene, xylene, and 1,3-butadiene.

In one embodiment, the adaptive gas sensor system comprises at least one transducer and/or gas sensor. In another embodiment, the at least one transducer and/or gas sensor comprises at least two operational modes. In a further embodiment, the at least two operational modes are at least two operating temperatures. It is to be understood that the at least two operational modes for the adaptive sensor system need not be operating temperatures, but may be any condition that is input into the at least one transducer and/or gas sensor in response to changes in the sensor signal output. Examples of such conditions include, without limitation, a temperature increase, a temperature decrease, an increase in humidity, a decrease in humidity, an electrical current, a change in pressure, a change in electromagnetic irradiation, and combinations thereof.

Where the adaptive gas sensor system comprises at least one transducer and/or gas sensor comprising at least two operational modes, a first operational mode controls the at least one transducer and/or gas sensor from a baseline level through analyte detection and initiation of a recovery phase upon analyte withdrawal, and a second operational mode controls the at least one transducer and/or gas sensor after the initiation of the recovery phase to temporarily change conditions of the at least one transducer and/or gas sensor to (i) accelerate removal of the analyte from the at least one transducer and/or gas sensor and (ii) accelerate recovery of the at least one transducer and/or gas sensor output towards the baseline level, wherein the microprocessor switches the at least one transducer and/or gas sensor from the first operational mode to the second operational mode in real-time and the temporary conditions of the second operational mode prevent the at least one transducer and/or gas sensor from detecting the analyte during the second operational mode. Upon completion of the temporary conditions of the second operational mode, the at least one transducer and/or gas sensor switches back to the first operational mode and/or one or more additional operational modes to complete recovery of the gas sensor towards the baseline level.

In another embodiment, the adaptive gas sensor system further comprises a microprocessor that communicates with the at least one transducer and/or gas sensor. In a further embodiment, the microprocessor is programmed with an algorithmic function that defines the conditions for the real-time switching between the at least two operational modes. Examples of such defining algorithmic functions include, without limitation, a time limitation, a signal output threshold for the analyte, a threshold rate of change of the output signal, a signal output pattern, a signal output frequency spectrum, and combinations thereof. For example, the initiation of the recovery phase of the first operational mode may be defined by an algorithm selected from a minimum threshold rate of change of an output signal from the gas sensor, a signal output threshold for the analyte, a signal output pattern, a signal output frequency spectrum, and combinations thereof. In a similar vein, the temporary conditions of the second operational mode may be defined by an algorithm selected from a time limitation on recovery after analyte withdrawal, a maximum threshold rate of change of an output signal from the gas sensor, a signal output pattern, a signal output frequency spectrum, and combinations thereof.

For comparative purposes, the following discussion describes the difference between a conventional MOS sensor system and an adaptive sensor system; however, as described above, it is to be understood that the adaptive sensor system is not limited to application on MOS sensors and may be used with any type of gas sensor to detect a target analyte.

Conventional MOS sensor systems operate at a fixed temperature (T1) that is optimized to a guarantee maximum signal change upon exposure to a given analyte. FIG. 1 shows how sensor resistance operates in a conventional MOS sensor. With reference to FIG. 1, in the absence of an analyte, the sensor signal settles on a stable baseline value of resistance (A). When the MOS sensor is exposed to an analyte (initiation is shown at B and the full exposure period is shown on the top line of the graph), the resistance of the MOS sensor changes (B→C) and approaches a new stable value (C→D) over a short timescale (also referred to as the response time). When the analyte is removed (D), the sensor signal slowly recovers to the baseline value over a much longer timescale (D→E). As an example, response time (B→C) could be as fast as 3 minutes and recovery time (D→E) could be as slow as 20 minutes.

Unlike conventional MOS sensor systems, which have a single operational temperature (T1 in FIG. 1), an adaptive sensor system equipped with a MOS gas sensor operates with at least two separate temperatures (also referred to herein as operational modes): a temperature that maximizes the sensor response to an analyte (operational mode 1) and a temperature that minimizes the recovery time of the sensor once the analyte has been removed (operational mode 2). When the recovery period of the sensor is complete, the sensor switches back to operational mode 1 (or to one or more additional operational modes) where the sensor will be ready to measure the next analyte. By using at least two operational modes, a sensor used in the adaptive sensor system is not subject to the slow recovery period of conventional MOS sensors.

Figure 2:
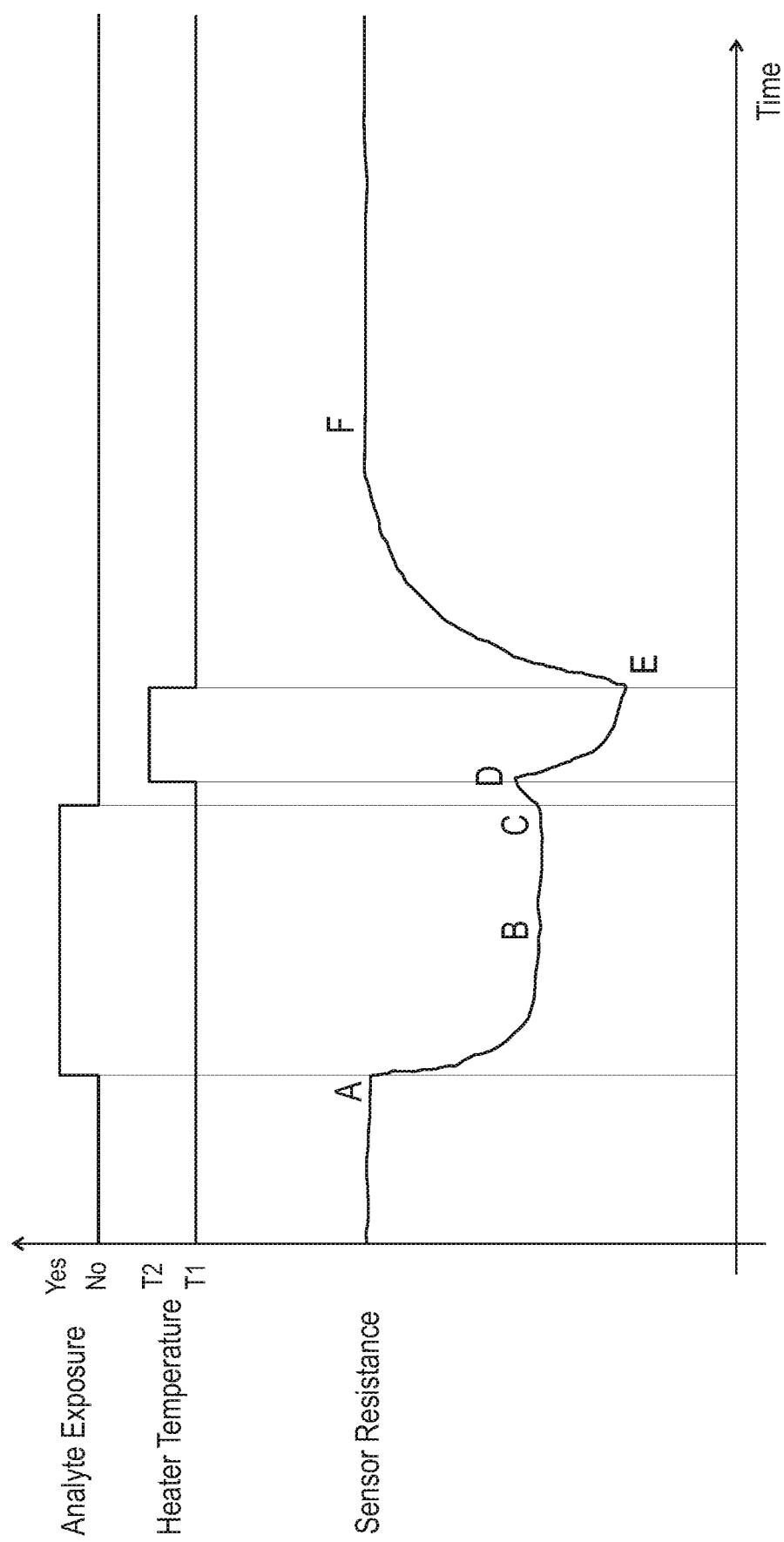
FIG. 2 is a graph showing analyte exposure, heater temperature, and sensor resistance over time for an adaptive gas sensor system as described herein.

FIG. 2 shows an operational profile of an adaptive sensor system that uses two temperature profiles as the operational modes. The baseline temperature T1 is the optimal temperature for detection of a particular analyte (T1 is operational mode 1), which is measured via sensor resistance and visualized via a sensor output signal. The sensor is exposed to the analyte at A and detects the presence of the analyte at T1 from A→C. After removal of the analyte at C, the sensor detects the beginning of a recovery phase from C→D and automatically switches to T2, which is the optimal temperature for recovery (T2 is operational mode 2). While the sensor is less responsive to the environment at T2 (D→E) than it is at T1 (A→D and E→F), the T2 temperature accelerates the desorption of the analyte, removing it from the sensing surface at an accelerated rate.

In one embodiment, the adaptive temperature control system comprises a microprocessor programmed with an algorithm that provides predetermined thresholds for switching the temperature of the gas sensor from T1→T2 and back to T1. With reference to FIG. 2, the algorithm automatically switches the temperature of the gas sensor from T1→T2 upon detection of the beginning of the recovery phase through an increase in sensor resistance after analyte withdrawal (C→D). In operation, such increase may be visually identified by an increase in the slope of the sensor resistance. Similarly, the algorithm automatically switches the temperature of the gas sensor back to T1 (the baseline temperature level) when the sensor resistance signal reaches or drops below a certain signal output threshold (e.g., FIG. 2, E) or after a fixed time period (e.g., thirty seconds or one minute). After the sensor has returned to T1, the sensor signal will begin transitioning towards the original baseline level (F). As a result of the time spent at T2, the overall recovery time (C→F) will be shorter than the recovery time observed using conventional operation (c.f., C→E in FIG. 1). As an example, in FIG. 2, the response time (A→B) could be 3 minutes while the recovery time (C→F) could be 10 minutes.

In another embodiment, the direction of the sensor response to the analyte may be positive or negative with respect to the baseline, depending on the sensing technology, materials, interaction mechanisms, and/or redox properties of the analyte. In FIG. 2, the response to the analyte is shown as negative to the baseline value at A. In a further embodiment, the sensor signal may increase, decrease, or remain stable with changes in the operational temperature of the gas sensor, i.e., from T1→T2 and from T2→T1. FIG. 2 shows the sensor signal decreasing in response to the temperature change from T1→T2 and increasing upon return of the temperature to the baseline temperature T1.

Figure 3:
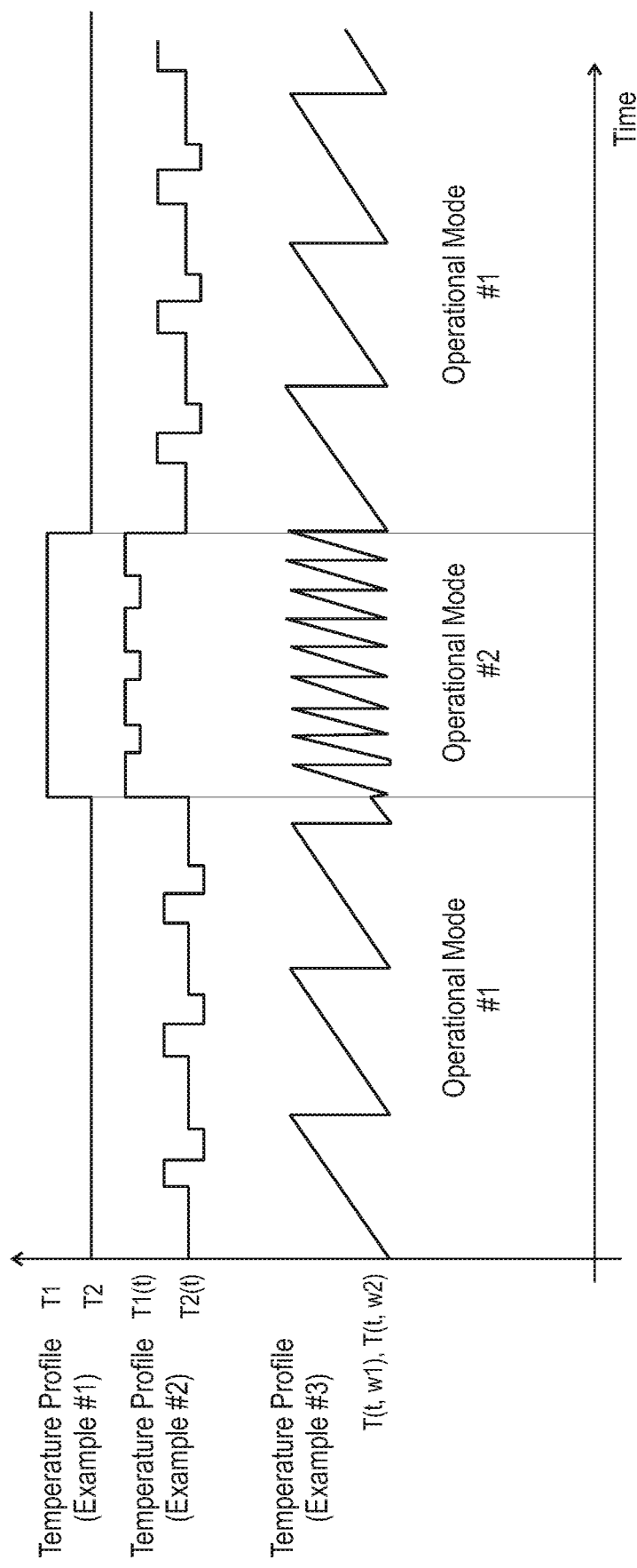
FIG. 3 is a graph showing three different temperature profiles as applied with two operational modes on an adaptive gas sensor system as described herein.

The two operational modes for the adaptive sensor system are independent of each other. The values of the two operational modes can be two separate fixed values (e.g., temperature values) or two separate arbitrary waveforms. Examples of waveform values include, without limitation, step, sawtooth, and sinusoidal functions. In FIG. 3, independent fixed temperature profiles for two operational modes are shown at the top line; independent stepped temperature profiles for two operational modes are shown at the middle line; and independent sawtooth temperature profiles for two operational modes are shown at the bottom line. With the stepped and sawtooth temperature profiles, the difference in the operational modes is not just the two separate temperature values (T1 and T2), but it is also the frequency of the waveforms (w1 and w2).

Figure 4:
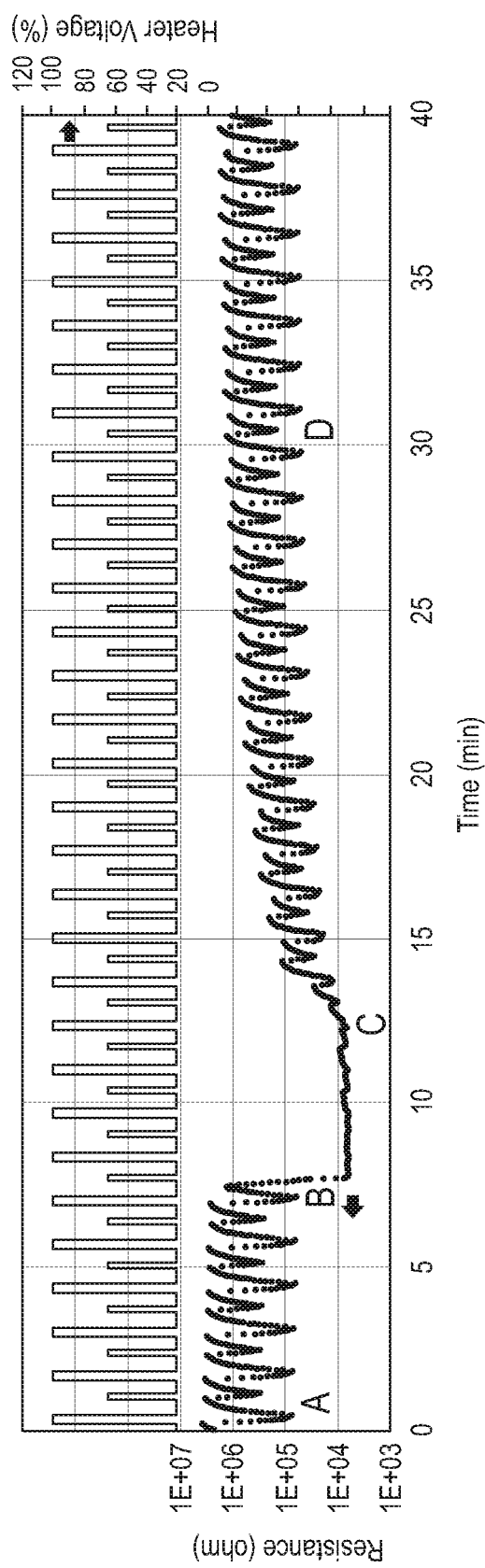
FIG. 4 is a graph showing analyte exposure and sensor recovery (y-axis resistance) over time for an ethanol vapor sample on a conventional MOS sensor with a single temperature operational mode (y-axis heater voltage).
Figure 5:
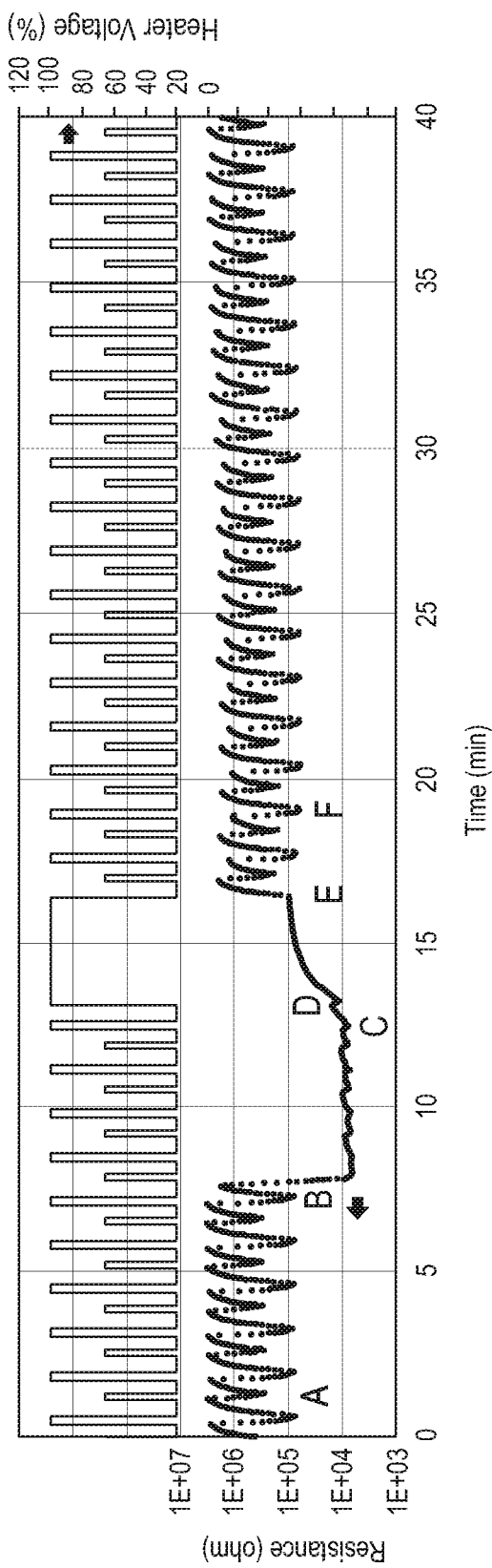
FIG. 5 is a graph showing analyte exposure and sensor recovery (y-axis resistance) over time for an ethanol vapor sample on an adaptive gas sensor operated with two temperature control operational modes (y-axis heater voltage).

FIG. 4, which is described in Example 1, shows the gas sensing results of a conventional MOS sensor system operated with a step function algorithm for a single temperature profile. FIG. 5, which is described in Example 2 shows the gas sensing results for an adaptive temperature control system operated with a step function algorithm for operational mode 1 (A→D and E→F) and a constant temperature algorithm for operational mode 2 (D→E). In FIG. 4, the analyte is introduced into the conventional MOS sensor system at B and is removed at C. The recovery period from C→D takes over 15 minutes and even at D, the conventional MOS sensor system never recovers fully to its baseline level (comparable to the baseline values at A). In FIG. 5, the adaptive temperature control system, which is in operational mode 1 at A, has an analyte introduced at B and removed at C. At D, the system senses the beginning of a recovery period and automatically switches to operational mode 2, which is operated with the constant temperature algorithm. At E, the system senses completion of the recovery period and switches back to operational mode 1. At F, the system returns to operational mode 1 because all traces of the analyte have been removed from the surface of the gas sensitive film and thus, the adaptive temperature control system is able to return to its baseline level. The recovery period C→F for the adaptive temperature control system takes approximately 10 minutes.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by volume, temperature is degrees centigrade, and pressure is at or near atmospheric. All components were obtained commercially unless otherwise indicated.

Comparative Example 1

Conventional MOS Sensor

Analyte Detection and Sensor Recovery

A commercial MOS sensor (Gas Sensor Element GGS 2330, UST Umweltsensortechnik GmbH, Geschwenda, Germany) was set up with a single operational mode (Operational Mode 1) consisting of the following four temperature steps with $V_{max}$=2.7 V (the operational voltage recommended by the manufacturer):
1. $V_1$=100% $V_{max}$ for $t_1$=15 s
2. $V_2$=20% $V_{max}$ for $t_2$=30 s
3. $V_3$=100% $V_{max}$ for $t_3$=10 s
4. $V_4$=65% $V_{max}$ for $t_4$=25 s The sensor was placed in an enclosed chamber with an air flow pump (Model B.1F15E1.A12VDC, Parker Hannifin Corp., Mayfield Heights, Ohio, USA) located downstream from the chamber. The air flow pump was set to deliver a rate of flow of 500 sscm.

The results of this experiment are shown graphically in FIG. 4. With reference to FIG. 4, a baseline value for the sensor was established with a flow of non-filtered air for approximately 7 minutes from t=0 min (A) to t=~7 min (B). The signal produced from A→B showed that the sensor was responding to the flow of non-filtered air. The analyte was introduced into the sensor via the air flow generated by the pump. The sensor was operated according to the four-step temperature settings of the single operational mode. At t~7 min (B), the sensor was exposed for approximately 5 minutes (B→C) to the vapors collected from the headspace of a 20 mL sample vial containing about 5 mL of white wine (primary components water and ethanol). Within a few seconds of exposure to the wine vapors, the resistance of the MOS sensor dropped rapidly as the ethanol vapors from the sample were adsorbed onto the MOS. At t~12 min (C), the vapor flow from the wine sample was stopped and the flow into the sensor was reverted back to the non-filtered air. Within a few seconds of the switch from the sample back to the air (C), the resistance of the MOS sensor started to increase towards the initial resistance level as the ethanol vapors from the sample were desorbed from the MOS. The resistance of the MOS sensor then recovered over a time scale of 17-18 minutes (C→D).

Example 2

Adaptive Sensor System

Analyte Detection and MOS Sensor Recovery

The same commercial MOS sensor used in example 1 was set up with two operational modes as follows with $V_{max}$=2.7 V:

Operational Mode 1 (optimized for sensing with four temperature steps):
1. $V_1$=100% $V_{max}$ for $t_1$=15 s
2. $V_2$=20% $V_{max}$ for $t_2$=30 s
3. $V_3$=100% $V_{max}$ for $t_3$=10 s
4. $V_4$=65% $V_{max}$ for $t_4$=25 s Operational Mode 2 (optimized for recovery with one step at a fixed temperature):
1. $V_{OP2}$=100% $V_{max}$ for $t_{OP2}$=3 min The sensor was placed in an enclosed chamber and was set up with the same air flow pump downstream from the sensor and the same rate flow (500 sscm) that was used in Example 1.

The results of this experiment are shown graphically in FIG. 5. With reference to FIG. 5, a baseline value for the sensor was established with a flow of non-filtered air for approximately 7 minutes from t=0 min (A) to t=~7 min (B). The signal produced from A→B showed that the sensor was responding to the flow of non-filtered air. At t~7 min (B), the sensor was exposed for approximately 5 minutes (B→C) to the vapors collected from the headspace of a 20 mL sample vial containing about 5 mL of white wine (primary components water and ethanol). Within a few seconds of exposure to the wine vapors, the resistance of the MOS sensor dropped rapidly as the ethanol vapors from the sample were adsorbed onto the MOS. At t~12 min (C), the vapor flow from the wine sample was stopped and the flow into the sensor was reverted back to the non-filtered air. Within a few seconds of the switch from the sample back to the air, the resistance of the MOS sensor started to increase (D) as the ethanol vapors from the sample were desorbed from the MOS. The initial increase at (D) was detected by the sensor triggering the switch from the four-temperature Operational Mode 1 to the fixed temperature Operational Mode 2, which was maintained for approximately 3 minutes, at which time the sensor was reverted back to Operational Mode 1 (t=~17 min). During Operational Mode 2 (D→E), the sensor output was not as sensitive to changes in the environment (when compared to Operational Mode 1), which allowed the sensor output to rapidly revert back to a level close to the initial baseline level (E→F), thus, shortening the recovery period from approximately 17-18 minutes (Example 1, C→D) to approximately 5 minutes (this Example, C→F).

We claim:
1. A gas sensor system comprising:
a gas sensor for detecting an analyte; and
a microprocessor programmed to control the gas sensor with at least two operational modes,
wherein,
a first operational mode controls the gas sensor from a baseline level through analyte detection and initiation of a recovery phase upon analyte withdrawal, wherein the initiation of the recovery phase comprises an increase in sensor resistance after the analyte withdrawal, and
a second operational mode temporarily changes conditions of the gas sensor after the initiation of the recovery phase to (i) accelerate removal of the analyte from the gas sensor and (ii) accelerate recovery of the gas sensor output towards the baseline level, wherein the microprocessor switches the gas sensor from the first operational mode to the second operational mode in real-time after a fixed time period or when the sensor resistance signal reaches or drops below a signal output threshold and the temporary conditions of the second operational mode prevent the gas sensor from detecting the analyte during the second operational mode.

2. The gas sensor system of claim 1, wherein upon completion of the temporary conditions of the second operational mode, the gas sensor switches back to the first operational mode and/or one or more additional operational modes to complete recovery of the gas sensor towards the baseline level.

3. The gas sensor system of claim 2, wherein identification of the completion of the temporary conditions is programmed into the microprocessor with an algorithmic function that defines one or more conditions selected from the group consisting of a time limitation on recovery after analyte withdrawal, a maximum threshold rate of change of an output signal from the gas sensor, a signal output pattern, a signal output frequency spectrum, and combinations thereof.

4. The gas sensor system of claim 1, wherein identification of the initiation of the recovery phase is programmed into the microprocessor with an algorithmic function that defines one or more conditions selected from the group consisting of a minimum threshold rate of change of an output signal from the gas sensor, a signal output threshold for the analyte, a signal output pattern, a signal output frequency spectrum, and combinations thereof.

5. The gas sensor system of claim 1, wherein the temporary change in conditions of the gas sensor is selected from the group consisting of a change in temperature, a change in humidity, an electrical current, a change in pressure, a change in electromagnetic irradiation, and combinations thereof.

6. The gas sensor system of claim 1, wherein the at least two operational modes are at least two operating temperatures with different temperature profiles.

7. The gas sensor system of claim 6, wherein the different temperature profiles are separate fixed temperature values and/or separate arbitrary waveforms.

8. The gas sensor system of claim 1, wherein the gas sensor comprises a material selected from the group consisting of metal oxide semiconductors, conducting polymers, non-conducting polymers, carbon nanotubes, oxidized graphene, sulfides, selenides, black phosphorus, phosphorene, germanene, silicone, and combinations thereof.

9. The gas sensor system of claim 8, wherein the gas sensor further comprises an additive selected from the group consisting of platinum, palladium, gold, rhodium, and combinations thereof.

10. The gas sensor system of claim 1, wherein the analyte is a gas selected from the group consisting of carbon monoxide (CO), carbon dioxide ($CO_2$), nitrogen oxides ($N_xO_y$; $x \geq 0$, $y \geq 0$), ammonia ($NH_3$), sulfur dioxide ($SO_2$), volatile organic compounds (VOCs), and combinations thereof.

11. A gas sensor system comprising:
a gas sensor for detecting an analyte; and
a microprocessor programmed to control the gas sensor with at least two operating temperatures,
wherein,
a first operating temperature controls the gas sensor from a baseline level through analyte detection and initiation of a recovery phase upon analyte withdrawal, wherein the initiation of the recovery phase comprises an increase in sensor resistance after the analyte withdrawal, and
a second operating temperature temporarily changes conditions of the gas sensor after the initiation of the recovery phase to (i) accelerate removal of the analyte from the gas sensor and (ii) accelerate recovery of the gas sensor output towards the baseline level, wherein the microprocessor switches the gas sensor from the first operating temperature to the second operating temperature in real-time after a fixed time period or when the sensor resistance signal reaches or drops below a signal output threshold and the temporary conditions of the second operating temperature prevent the gas sensor from detecting the analyte while at the second operating temperature.

12. The gas sensor system of claim 11, wherein upon completion of the temporary conditions of the second operating temperature, the gas sensor switches back to the first operating temperature and/or one or more additional operating temperatures to complete recovery of the gas sensor towards the baseline level.

13. The gas sensor system of claim 12, wherein identification of the completion of the temporary conditions is programmed into the microprocessor with an algorithmic function that defines one or more conditions selected from the group consisting of a time limitation on recovery after analyte withdrawal, a maximum threshold rate of change of an output signal from the gas sensor, a signal output pattern, a signal output frequency spectrum, and combinations thereof.

14. The gas sensor system of claim 11, wherein identification of the initiation of the recovery phase is programmed into the microprocessor with an algorithmic function that defines one or more conditions selected from the group consisting of a minimum threshold rate of change of an output signal from the gas sensor, a signal output threshold for the analyte, a signal output pattern, a signal output frequency spectrum, and combinations thereof.

15. The gas sensor system of claim 11, wherein the temporary change in conditions of the gas sensor is selected from the group consisting of a change in temperature, a change in humidity, an electrical current, a change in pressure, a change in electromagnetic irradiation, and combinations thereof.

16. The gas sensor system of claim 11, wherein the at least two operational temperatures have different temperature profiles.

17. The gas sensor system of claim 16, wherein the different temperature profiles are separate fixed temperature values and/or separate arbitrary waveforms.

* * * * *